United States Patent
Nguyen et al.

(10) Patent No.: US 10,398,811 B1
(45) Date of Patent: Sep. 3, 2019

(54) MEDICAL IRRIGATION SYSTEM

(71) Applicant: The Board of Regents of the University of Nebraska, Lincoln, NE (US)

(72) Inventors: Thang Nguyen, Elkhorn, NE (US); Michael Wadman, Omaha, NE (US); Richard Morris, Omaha, NE (US); Vincent Morris, Omaha, NE (US)

(73) Assignee: Board of Regents of the University of Nebraska, Lincoln, NE (US)

( * ) Notice: Subject to any disclaimer, the term of this patent is extended or adjusted under 35 U.S.C. 154(b) by 0 days.

(21) Appl. No.: 15/662,734

(22) Filed: Jul. 28, 2017

Related U.S. Application Data

(60) Provisional application No. 62/367,771, filed on Jul. 28, 2016.

(51) Int. Cl.
*A61M 1/00* (2006.01)

(52) U.S. Cl.
CPC ........ *A61M 1/0064* (2013.01); *A61M 1/0001* (2013.01); *A61M 1/0031* (2013.01); *A61M 1/0041* (2013.01)

(58) Field of Classification Search
CPC .............. A61M 1/0064; A61M 1/0001; A61M 1/0031; A61M 1/0041
See application file for complete search history.

(56) References Cited

U.S. PATENT DOCUMENTS

| | | | |
|---|---|---|---|
| 6,562,013 B1 | 5/2003 | Marasco, Jr. | |
| 7,802,574 B2 | 9/2010 | Schultz | |
| 2008/0154183 A1* | 6/2008 | Baker | A61M 1/0058 604/28 |
| 2009/0012483 A1* | 1/2009 | Blott | A61M 1/0088 604/315 |
| 2013/0331772 A1* | 12/2013 | Vogt | B05B 7/2421 604/24 |

OTHER PUBLICATIONS https://www.bionix.com/medicaltech/product/igloo-wound-irrigation-system/.
http://www.zimmerbiomet.com/medical-professionals/surgical-and-operating-room-solutions/product/pulsavac-plus-products.html.
https://www.stryker.com/content/stryker/us/en/surgical/products/interpulse-pulsed-lavage-system.html.

\* cited by examiner

*Primary Examiner* — Amber R Stiles
(74) *Attorney, Agent, or Firm* — Suiter Swantz pc llo

(57) ABSTRACT

Medical wound irrigation systems are described that may be used in environments such as hospitals and first aid stations, and for military applications, e.g., for medics and along transport routes for the wounded. The irrigation systems can provide continuous variable pressure for irrigating a wound. For example, in some embodiments, a medical irrigation system can be used to provide a steady pressure level while irrigating about one liter of solution in less than about one minute, e.g., to assist during wound irrigation and debridement. The medical irrigation system may include an air-powered irrigation device, which pressurizes an irrigation solution, such as a cleansing fluid, to create an ejection force. In some embodiments, the medical irrigation system can include a replaceable bottle cap with an inlet for connecting to a source of pressurized fluid (e.g., pressurized gas, such as pressurized air) and an outlet for the irrigation solution/cleansing fluid.

20 Claims, 8 Drawing Sheets

MEDICAL IRRIGATION SYSTEM

CROSS-REFERENCE TO RELATED APPLICATIONS

The present application claims the benefit under 35 U.S.C. § 119(e) of U.S. Provisional Application Ser. No. 62/367,771, filed Jul. 28, 2016, and titled "Continuous Variable Pressure Wound Irrigation System," which is herein incorporated by reference in its entirety.

BACKGROUND

For a wound to properly heal, the afflicted area must be completely clean. Inadequate wound irrigation is often the precursor to complications such as poor healing, infection, or cross contamination.

DRAWINGS

The Detailed Description is described with reference to the accompanying figures. The use of the same reference numbers in different instances in the description and the figures may indicate similar or identical items.

DETAILED DESCRIPTION

Figure 1A:
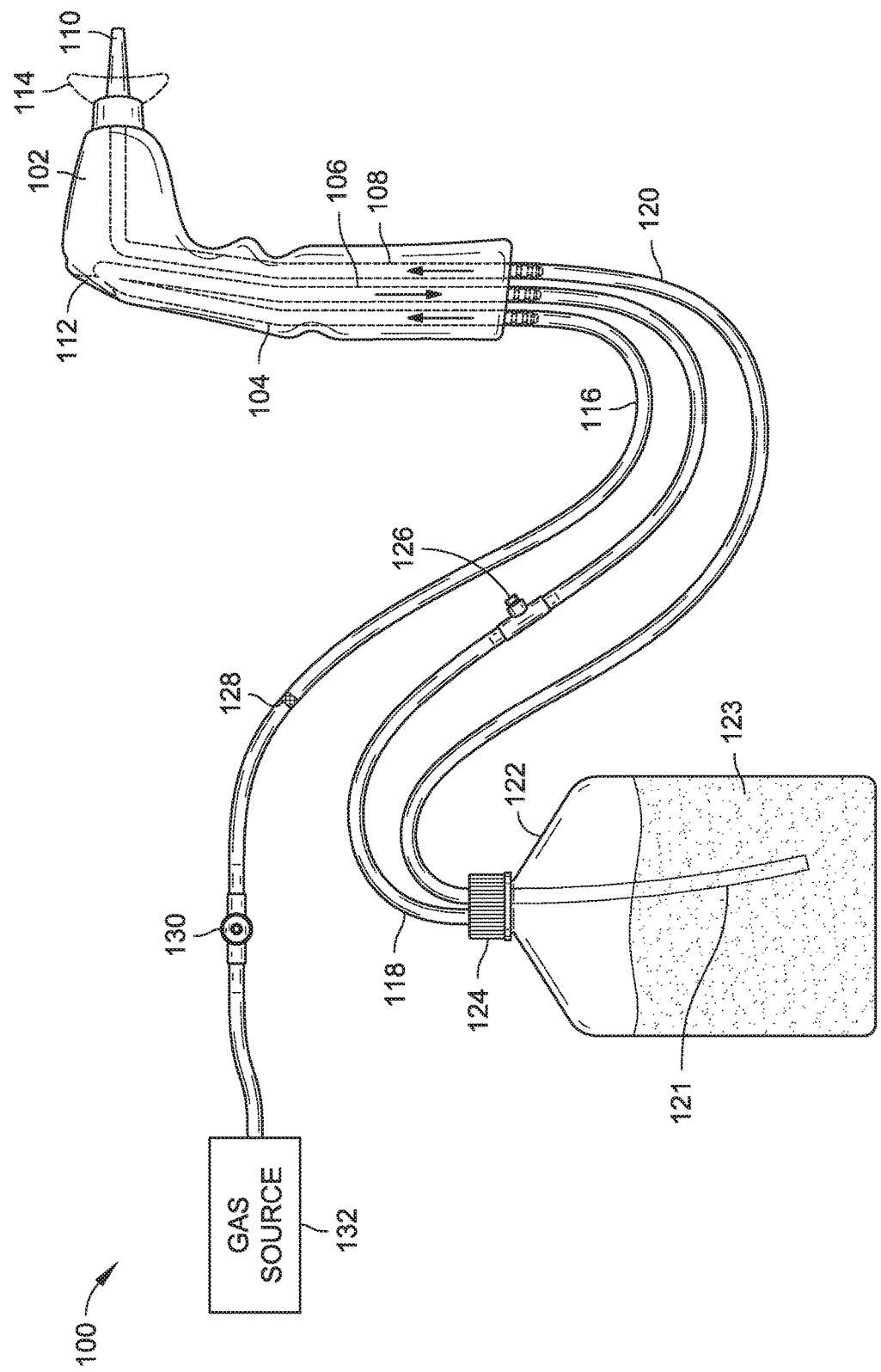
FIG. 1A is a diagrammatic illustration of a wound irrigation system in accordance with an example embodiment of the present disclosure.
Figure 1C:
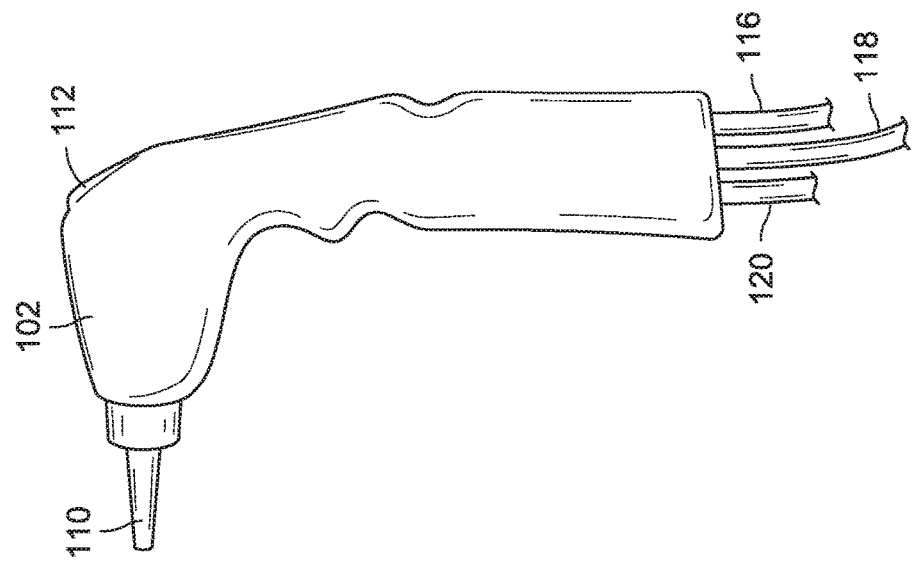
FIG. 1C is a further diagrammatic illustration of the wound irrigation system illustrated in FIG. 1A.
Figure 1B:
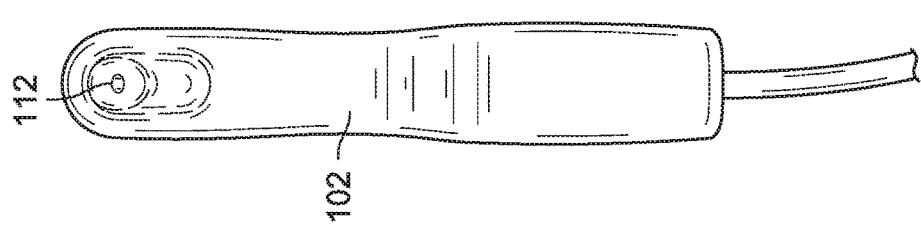
FIG. 1B is another diagrammatic illustration of the wound irrigation system illustrated in FIG. 1A.

Oftentimes injuries occur in the field, and patients are initially treated by first responders, such as paramedics or firemen. Generally, two factors are important to optimally clean a wound: the amount of pressure used to irrigate the wound, and the amount of irrigation solution used. These two factors may vary greatly between providers (e.g., due to different levels of training, equipment, time, and so forth). Complicating matters, sometimes removal of an offending skin or wound irritant, such as a chemical, can be time sensitive. The irrigation process for a wound is often accomplished using sterile water or normal saline that is sprayed into the wound via a ten milliliter (10 ml) or larger syringe. According to a clinical procedure manual by Roberts & Hedges, this method may produce approximately twenty-five to forty pounds per square inch (25-40 psi) of water pressure, e.g., if a medical provider is pushing on the syringe plunger with both hands, with a consistent amount of force, and using proper equipment. However, in practice, such techniques may produce a wide range of water pressures, e.g., depending on how hard a provider pushes on the syringe plunger. Moreover, in cases of deep wound irrigation, a desired amount of water pressure may be significantly higher and thus harder to consistently achieve. Powered irrigation devices typically depend on an electrical power source and are not adaptable to multiple water sources.

Referring generally to FIGS. 1 through 6D, medical wound irrigation systems are described. The wound irrigation systems may be used in environments such as hospitals and first aid stations, and for military applications, e.g., for medics in the field, along transport routes for wounded war fighters, and so forth. The irrigation systems can provide continuous variable pressure for irrigating a wound. For example, in some embodiments, a medical irrigation system can be used to provide a steady pressure level while irrigating about one liter of solution in less than about one minute, e.g., to assist during wound irrigation and debridement. The medical irrigation system may include an air-powered irrigation device, which pressurizes an irrigation solution, such as a cleansing fluid, to create an ejection force. In some embodiments, the medical irrigation system can include a replaceable bottle cap with an inlet for connecting to a source of pressurized fluid (e.g., pressurized gas, such as pressurized air) and an outlet for the irrigation solution/cleansing fluid.

Referring to FIGS. 1A through 1D, wound irrigation systems 100 are described. An irrigation system 100 includes an air-powered irrigation device configured as a handheld dispenser 102. Pressurized gas for the handheld dispenser 102 may be supplied from an in-room source of pressurized gas, such as an air/pressure source 132 that provides a continuous flow of gas, including, but not necessarily limited to, a medical piped oxygen system, such as a medical air valve available in a medical room and/or a military first aid station, a bag valve mask (BVM), a pressurized gas cartridge, and so on. In some embodiments, the handheld dispenser 102 may have a regulator port 112, which can be occluded by, for example, a digit on an operator's hand, such as a finger or a thumb. Once the air-powered irrigation device has been connected to the air/pressure source 132, the operator can initiate flow of an irrigation solution 123 (e.g., an isotonic solution, a saline solution) by occluding the regulator port 112 on the handheld dispenser 102. The operator may adjust the pressure by varying the amount of force applied by the digit and/or the coverage of the regulator port 112 by the digit.

In some embodiments, the irrigation solution 123 can be dispensed at a fluid pressure between about one pound per square inch (1 psi) and about sixty pounds per square inch (60 psi). However, it should be noted that this range of fluid pressure is provided by way of example and is not meant to limit the present disclosure. In other embodiments, the irrigation solution 123 can be dispensed at a fluid pressure less than about one pound per square inch (1 psi) and/or a fluid pressure greater than about sixty pounds per square inch (60 psi). In embodiments, the irrigation solution 123 can be dispensed at a fluid pressure of about one pound per square inch (1 psi) (e.g., for chemical decontamination), a fluid pressure between about eight pounds per square inch (8 psi) and about thirteen pounds per square inch (13 psi) (e.g., for wound irrigation to overcome adherence of foreign substances), a fluid pressure between about fourteen pounds per square inch (14 psi) and about eighteen pounds per square inch (18 psi) (e.g., for mildly contaminated wounds), a fluid pressure between about eighteen pounds per square inch (18 psi) and about twenty-five pounds per square inch (25 psi) (e.g., for grossly contaminated wounds), a fluid pressure between about fifty pounds per square inch (50 psi) and about sixty pounds per square inch (60 psi) (e.g., for clothes or closed skin), and so on.

Figure 1D:
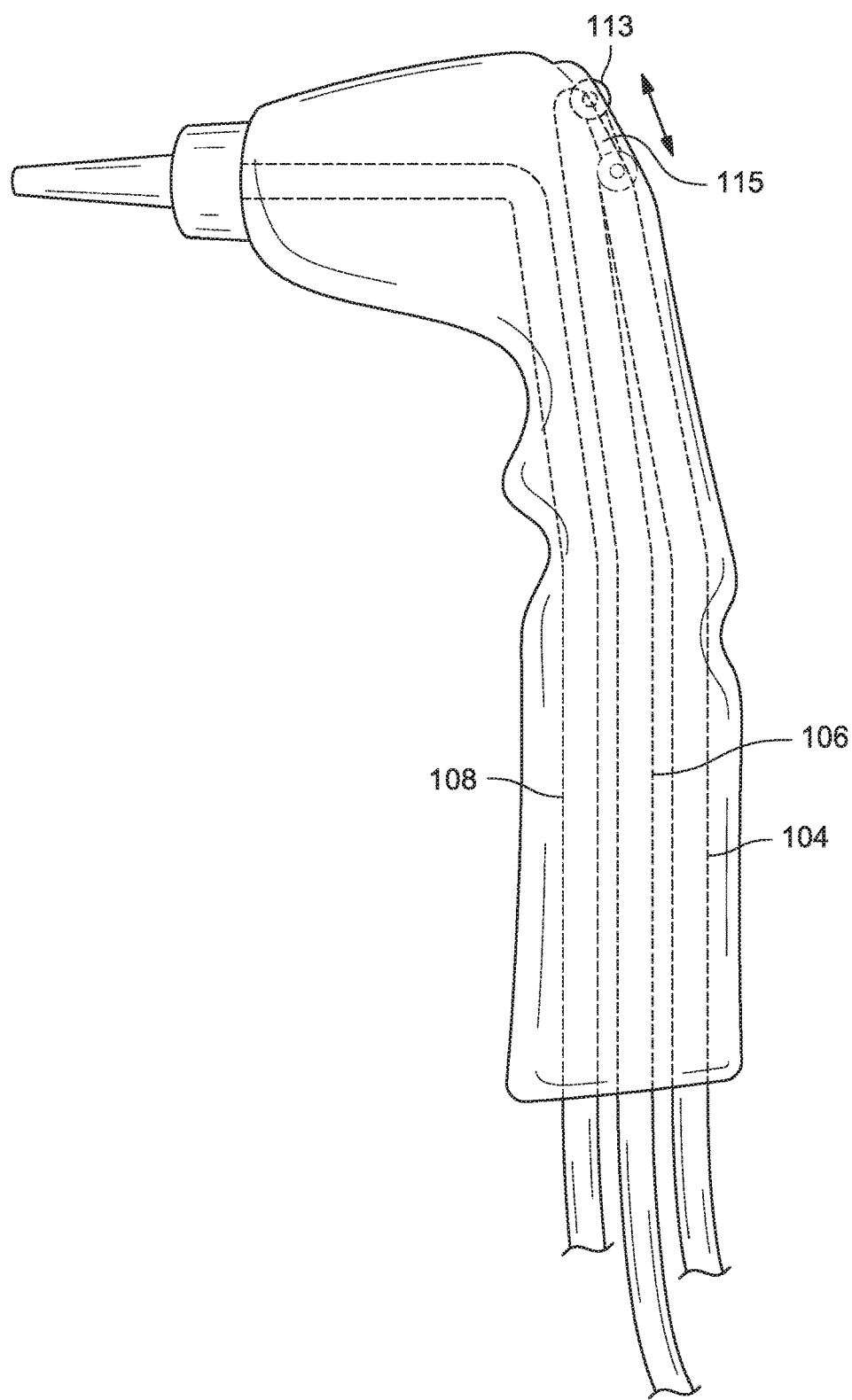
FIG. 1D is a diagrammatic illustration of another wound irrigation system in accordance with an example embodiment of the present disclosure.

With reference to FIG. 1D, in some embodiments, a flow rate controller, such as a roller actuator 113 on the handheld dispenser 102, may be used to adjust the amount of pressure, e.g., by occluding the regulator port 112. In this example, the operator can press or roll the roller actuator 113 distally or proximally with respect to the handheld dispenser 102 to occlude the regulator port 112 to varying degrees to set a desired pressure level. Pressure within the handheld dispenser 102 may resist movement of the roller actuator 113, allowing an operator to fine-tune how far the roller is moved to occlude the regulator port 112. In other embodiments, a biasing device, such as a spring, may be used to resist movement of the roller actuator 113. The roller may be guided to move along a track 115 within the handheld dispenser 102 (e.g., using an axle extending through the roller actuator 113 and traveling in the track 115). However, a roller is provided by way of example and is not meant to limit the present disclosure. In other embodiments, an actuator may be provided as a cam, a clamp, or another type of actuator designed to limit the flow of irrigation solution 123 by occluding the regulator port 112.

The irrigation system 100 may include an air line 116 and an air line 118 to deliver pressurized gas from the air/pressure source 132 to a container 122 holding the irrigation solution 123. The air lines 116 and 118 may be connected to channels 104 and 106, respectively, in the handheld dispenser 102 (e.g., via fittings such as barbs/Christmas tree connections protruding from the handheld dispenser 102). Together, the air lines 116 and 118 and the channels 104 and 106 form a fluid path coupling the container 122 with the air/pressure source 132, and the channels 104 and 106 form at least a portion of this fluid path. The irrigation system 100 may also include an irrigation solution line 120 to deliver the irrigation solution 123 from the container 122 to the handheld dispenser 102. The irrigation solution line 120 may be connected to a channel 108 in the handheld dispenser 102 (e.g., via a fitting such as a barb/Christmas tree connection protruding from the handheld dispenser 102). The channel 108 forms a fluid path between a nozzle of the handheld dispenser 102 and an input of the handheld dispenser 102 (e.g., the fitting protruding from the handheld dispenser 102). In this manner, the input can be fluidically coupled to the container 122. In some embodiments, the channels 104, 106, and/or 108 may be formed using medical-grade tubing. In this example, the roller actuator 113 may be a roller-clamp type actuator that can crimp the interface between connecting tubing segments of channels 104 and 106 to block (or at least partially block) the flow of pressurized gas through the handheld dispenser 102.

In other embodiments, the channels 104, 106, and/or 108 may be formed in and defined by the body of the handheld dispenser 102. In this example, the regulator port 112 may be formed as an aperture defined in the body of the handheld dispenser 102 and disposed between first and second portions of the fluid path including the channels 104 and 106 (e.g., in fluid communication with the channels 104 and 106), and the operator's digit and/or the roller actuator 113 can be used to occlude (e.g., to close or at least partially close) the aperture and increase an internal pressure of the container 122. For instance, the roller actuator 113 can at least partially narrow or widen a segment of the fluid path between the channels 104 and 106 when the roller translates over the segment in a first direction or a second direction. In some embodiments, the roller actuator 113 can be used to dispense the irrigation solution 123 at a number of different fluid pressures, e.g., ranging between about one pound per square inch (1 psi) and about sixty pounds per square inch (60 psi). In some embodiments, one or more air supply lines (e.g., the air line 116) may include an air filter, such as a filter 128 for filtering air from the air/pressure source 132 (e.g., to prevent or minimize infiltration of contaminants into the channels 104, 106, and/or 108, the air lines 116 and 118, the irrigation solution line 120, the container 122, and so forth). As described herein, an air filter may be configured as a high-efficiency particulate absorber, such as a high efficiency particulate air (HEPA) filter.

Once the container 122 is pressurized with air, the operator may start the flow of irrigation solution 123 by occluding air release at the irrigation handle. In some embodiments, the irrigation system 100 may limit the flow of pressurized gas from the air/pressure source 132 to not exceed, for instance, a maximum pressure in pounds per square inch (psi) (e.g., for optimal wound healing). For example, the handheld dispenser 102, the air line 116, the air line 118, and/or the container 122 may include an adjustable pressure release valve 126 or another pressure limiting mechanism. The pressure release valve 126 may be configured to prevent the internal pressure of the container 122 from exceeding, for instance, a threshold pressure. In some embodiments, the threshold pressure may be about twenty pounds per square inch (20 psi) or more. The irrigation system 100 may also include a flow control valve, e.g., using a dial knob 130 or another adjustment mechanism, to control the flow rate of gas from the air/pressure source 132.

In some embodiments, the irrigation system 100 includes an adaptor, such as a bottle cap 124, for the container 122. The adaptor may replace, for instance, a bottle cap included with a saline container. For example, the bottle cap 124 may be a universal fit cap for standard saline bottles. The bottle cap 124 may have inlet and outlet ports connected to the air line 118 and the irrigation solution line 120, respectively. The bottle cap 124 may also include collection tubing 121 for extending into the container 122 and collecting the irrigation solution 123. However, a saline bottle is provided by way of example and is not meant to limit the present disclosure. In other embodiments, the irrigation system 100 can include an adaptor configured to connect to other various fluid sources, including, but not necessarily limited to: an intravenous (IV) saline bag, a collapsible bottle, a refillable bottle, and so forth. In some embodiments, the handheld dispenser 102 and a container/bag for holding the irrigation solution 123 may be coupled together in a unitary device. For example, the container 122 for the irrigation solution 123 may be connected to a posterior end of the handheld dispenser 102 to prime the device.

The irrigation system 100 may also include a nozzle, such as a spray tip 110 on the handheld dispenser 102, for spraying the irrigation solution 123 and/or a splash shield 114 disposed proximate to and at least partially surrounding the nozzle for containing the irrigation solution 123 while it is sprayed from the handheld dispenser 102. The spray tip 110 may be one of a number of different interchangeable irrigation tips that provide various spray patterns and/or fluid pressure characteristics when expelling the irrigation solution 123 (e.g., as illustrated in FIGS. 6A through 6D). In some embodiments, differently shaped, sized, and/or patterned spray tips may be used to provide different spray patterns and/or fluid pressure characteristics. For example, a shower head-type nozzle as described with reference to FIG. 6A may be used to provide a lower pressure, wider flow in comparison to a higher pressure, narrower flow provided by a differently patterned, sized, and/or shaped nozzle, such as the nozzle described with reference to FIG. 6D. In some embodiments, a particular nozzle may be selected for decontamination for harmful industry, laboratory, and/or military materials (such as hazardous chemicals in a plant/laboratory, chemical weapons in a military situation, and so forth).

Figure 2:
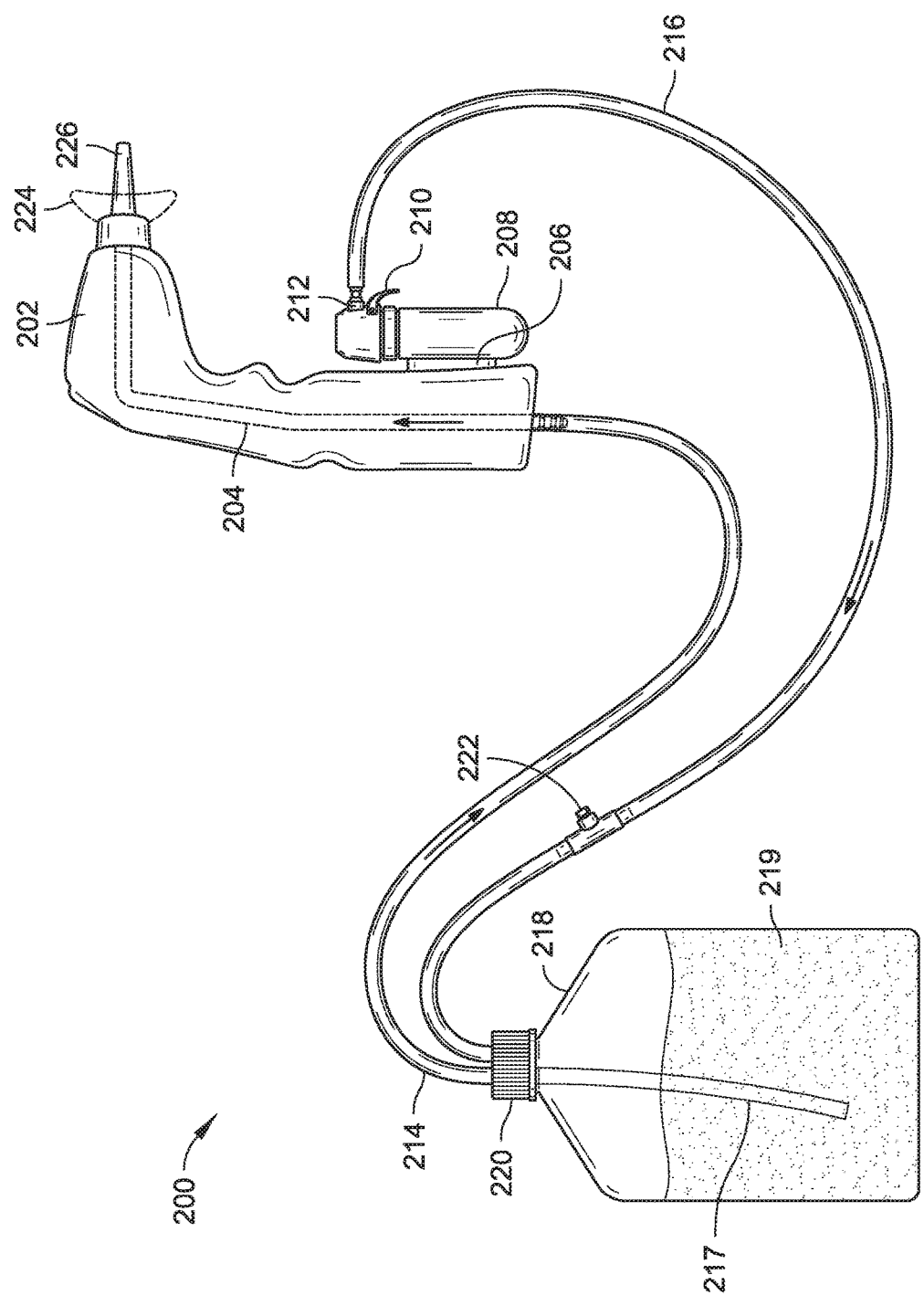
FIG. 2 is a diagrammatic illustration of a wound irrigation system in accordance with an example embodiment of the present disclosure.

Referring now to FIG. 2, an irrigation system 200 is described. In embodiments, pressurized gas for an air-powered irrigation device configured as a handheld dispenser 202 may be supplied from a portable and/or replaceable pressurized gas source, such as a pressurized carbon dioxide ($CO_2$) cartridge 208. As described herein, a $CO_2$ cartridge 208 can be used to pressurize and empty a one liter bottle of irrigation fluid, such as a container 218, in about three to four bursts of pressurized gas. The $CO_2$ cartridge 208 can be connected to the handheld dispenser 202 by a connector 206 (e.g., a holster), which may be positioned on a handle of the handheld dispenser 202 and include a fitting 212 (e.g., for an air line). The connector 206 may also include an actuator 210, such as a trigger or another actuation device (e.g., a button), to pressurize an irrigation solution 219 held in the container 218. Each trigger pull may deliver a measured dose of air into, for example, a saline bottle.

The irrigation system 200 may include an air line 216 to deliver pressurized gas from the $CO_2$ cartridge 208 to the container 218 holding the irrigation solution 219. The air line 216 forms a fluid path coupling the container 218 with the $CO_2$ cartridge 208. The irrigation system 200 may also include an irrigation solution line 214 to deliver the irrigation solution 219 from the container 218 to the handheld dispenser 202. The irrigation solution line 214 may be connected to a channel 204 in the handheld dispenser 202 (e.g., via a fitting protruding from the handheld dispenser 202). The channel 204 forms a fluid path between a nozzle of the handheld dispenser 202 and an input of the handheld dispenser 202 (e.g., the fitting protruding from the handheld dispenser 202). In this manner, the input can be fluidically coupled to the container 218. In some embodiments, the channel 204 may be formed using medical-grade tubing. In other embodiments, the channel 204 may be formed in and defined by the body of the handheld dispenser 202. In some embodiments, one or more air supply lines (e.g., the air line 216) may include an air filter for filtering air from the $CO_2$ cartridge 208 or from another source of pressurized gas.

Once activated, the $CO_2$ cartridge 208 pressurizes the irrigation solution 219, allowing an operator to release the irrigation solution 219, e.g., via an actuator on the handheld dispenser 202. The actuator may be similar to the actuator 304 described with reference to FIG. 3. In other embodiments, once the container 218 is pressurized with air, the flow of irrigation solution 219 may begin automatically. In some embodiments, flow volume and pressure may depend on a number of trigger presses. The irrigation system 200 may also limit the flow of carbon dioxide from the $CO_2$ cartridge 208 to not exceed, for instance, a maximum pressure in pounds per square inch (psi) (e.g., for optimal wound healing). For example, the connector 206, the air line 216, and/or the container 218 may include an adjustable pressure release valve 222 or another adjustable pressure limiting mechanism. The pressure release valve 222 may be configured to prevent the internal pressure of the container 218 from exceeding, for instance, a threshold pressure. In some embodiments, the threshold pressure may be about twenty pounds per square inch (20 psi) or more. In some embodiments, fluid pressure may be adjusted using a pressure gauge (e.g., on a distal end of the irrigation device).

In some embodiments, the irrigation system 200 includes an adaptor, such as a bottle cap 220, for the container 218. The adaptor may replace, for instance, a bottle cap included with a saline container. For example, the bottle cap 220 may be a universal fit cap for standard saline bottles. The bottle cap 220 may have inlet and outlet ports connected to the air line 216 and the irrigation solution line 214, respectively. The bottle cap 220 may also include collection tubing 217 for extending into the container 218 and collecting the irrigation solution 219. However, a saline bottle is provided by way of example and is not meant to limit the present disclosure. In other embodiments, the irrigation system 200 can include an adaptor configured to connect to other various fluid sources, including, but not necessarily limited to: an intravenous (IV) saline bag, a collapsible bottle, a refillable bottle, and so forth. In some embodiments, the handheld dispenser 202 and a container/bag for holding the irrigation solution 219 may be coupled together in a unitary device. For example, the container 218 for the irrigation solution 219 may be connected to a posterior end of the handheld dispenser 202 to prime the device. The irrigation system 200 may also include a nozzle, such as a spray tip 226 on the handheld dispenser 202, for spraying the irrigation solution 219 and/or a splash shield 224 disposed proximate to and at least partially surrounding the nozzle for containing the irrigation solution 219 while it is sprayed from the handheld dispenser 202. The spray tip 226 may be one of a number of different interchangeable irrigation tips that provide various spray patterns and/or fluid pressure characteristics when expelling the irrigation solution 219 (e.g., as illustrated in FIGS. 6A through 6D).

Figure 3:
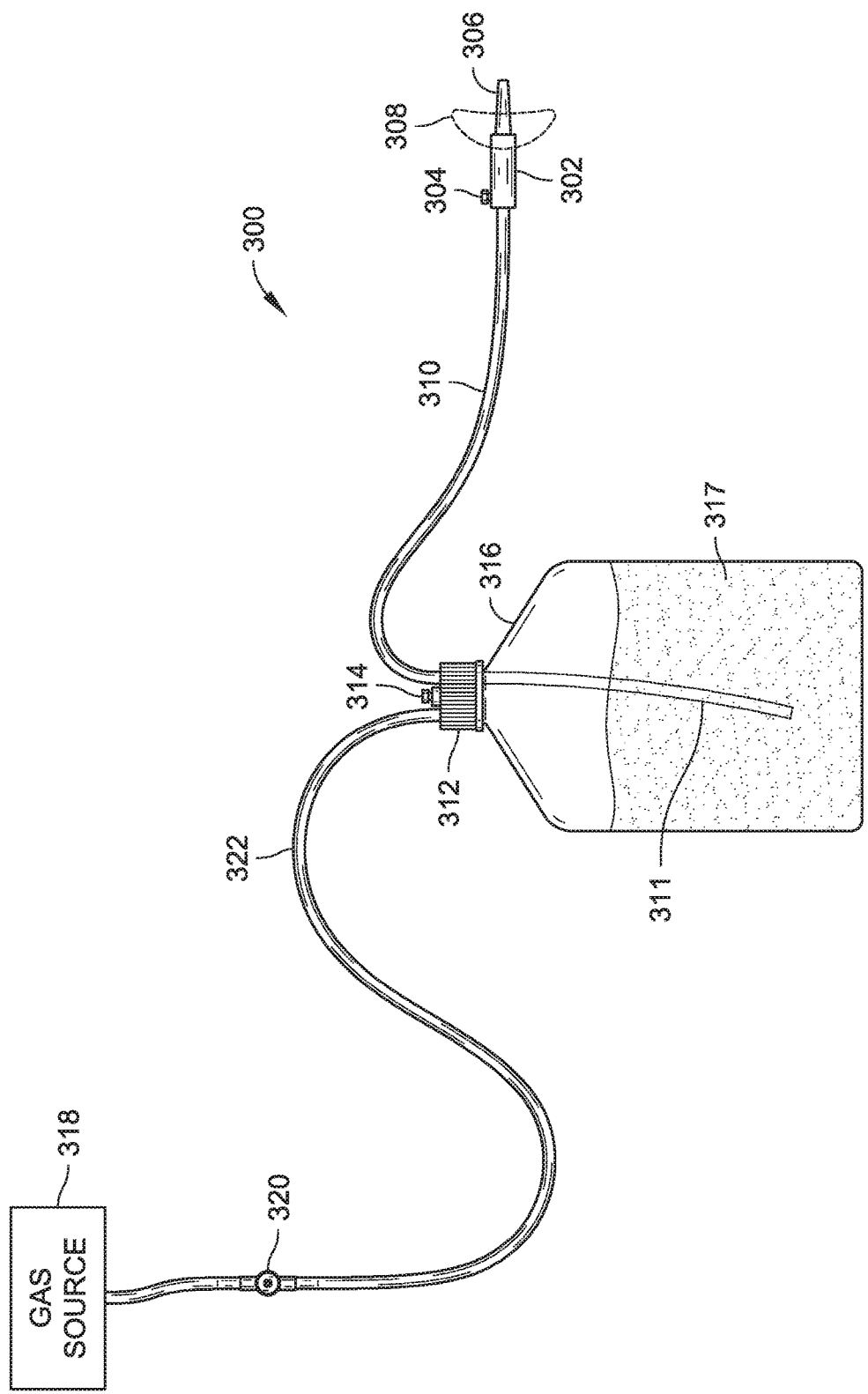
FIG. 3 is a diagrammatic illustration of another wound irrigation system in accordance with an example embodiment of the present disclosure.

Referring to FIG. 3, an irrigation system 300 is described. The irrigation system 300 includes an air-powered irrigation device configured as a handheld dispenser, such as an irrigation wand 302. Pressurized gas for the irrigation wand 302 may be supplied from an in-room source of pressurized gas, such as an air/pressure source 318 that provides a continuous flow of gas, including, but not necessarily limited to, a medical piped oxygen system, such as a medical air valve available in a medical room, a military first aid station, and so on. In some embodiments, the irrigation wand 302 may have an actuator 304, such as a button or another actuation device (e.g., a trigger), to initiate flow of an irrigation solution 317, e.g., once the air-powered irrigation device has been connected to the air/pressure source 318.

The irrigation system 300 may include an air line 322 to deliver pressurized gas from the air/pressure source 318 to a container 316 holding the irrigation solution 317. The air line 322 forms a fluid path coupling the container 316 with the air/pressure source 318. The irrigation system 300 may also include an irrigation solution line 310 to deliver the irrigation solution 317 from the container 316 to the irrigation wand 302. The irrigation solution line 310 may be connected to a channel in the irrigation wand 302 (e.g., via a fitting protruding from the irrigation wand 302). The channel forms a fluid path between a nozzle of the irrigation wand 302 and an input of the irrigation wand 302 (e.g., the fitting protruding from the irrigation wand 302). In this manner, the input can be fluidically coupled to the container 316. In some embodiments, the channel may be formed using medical-grade tubing. In other embodiments, the channel may be formed in and defined by the body of the irrigation wand 302. In some embodiments, one or more air supply lines (e.g., the air line 322) may include an air filter for filtering air from the air/pressure source 318 (e.g., to prevent or minimize infiltration of contaminants into the channel, the air line 322, the irrigation solution line 310, the container 316, and so forth).

Once the container 316 is pressurized with air, the operator may start the flow of irrigation solution 317 via the actuator 304. In some embodiments, the irrigation system 300 may limit the flow of pressurized gas from the air/pressure source 318 to not exceed, for instance, a maximum pressure in pounds per square inch (psi) (e.g., for optimal wound healing). For example, the irrigation wand 302, the air line 322, and/or the container 316 may include an adjustable pressure release valve 314 or another pressure limiting mechanism. The pressure release valve 314 may be configured to prevent the internal pressure of the container 316 from exceeding, for instance, a threshold pressure. In some embodiments, the threshold pressure may be about twenty pounds per square inch (20 psi) or more. The irrigation system 300 may also include a flow control valve, e.g., using a dial knob 320 or another adjustment mechanism, to control the flow rate of gas from the air/pressure source 318.

In some embodiments, the irrigation system 300 includes an adaptor, such as a bottle cap 312, for the container 316. The adaptor may replace, for instance, a bottle cap included with a saline container. For example, the bottle cap 312 may be a universal fit cap for standard saline bottles. The bottle cap 312 may have inlet and outlet ports connected to the air line 322 and the irrigation solution line 310, respectively. The bottle cap 312 may also include collection tubing 311 for extending into the container 316 and collecting the irrigation solution 317. However, a saline bottle is provided by way of example and is not meant to limit the present disclosure. In other embodiments, the irrigation system 300 can include an adaptor configured to connect to other various fluid sources, including, but not necessarily limited to: an intravenous (IV) saline bag, a collapsible bottle, a refillable bottle, and so forth. In some embodiments, the irrigation wand 302 and a container/bag for holding the irrigation solution 317 may be coupled together in a unitary device. For example, the container 316 for the irrigation solution 317 may be connected to a posterior end of the irrigation wand 302 to prime the device. The irrigation system 300 may also include a nozzle, such as a spray tip 306 on the irrigation wand 302, for spraying the irrigation solution 317 and/or a splash shield 308 disposed proximate to and at least partially surrounding the nozzle for containing the irrigation solution 317 while it is sprayed from the irrigation wand 302. The spray tip 306 may be one of a number of different interchangeable irrigation tips that provide various spray patterns and/or fluid pressure characteristics when expelling the irrigation solution 317 (e.g., as illustrated in FIGS. 6A through 6D).

Figure 4:
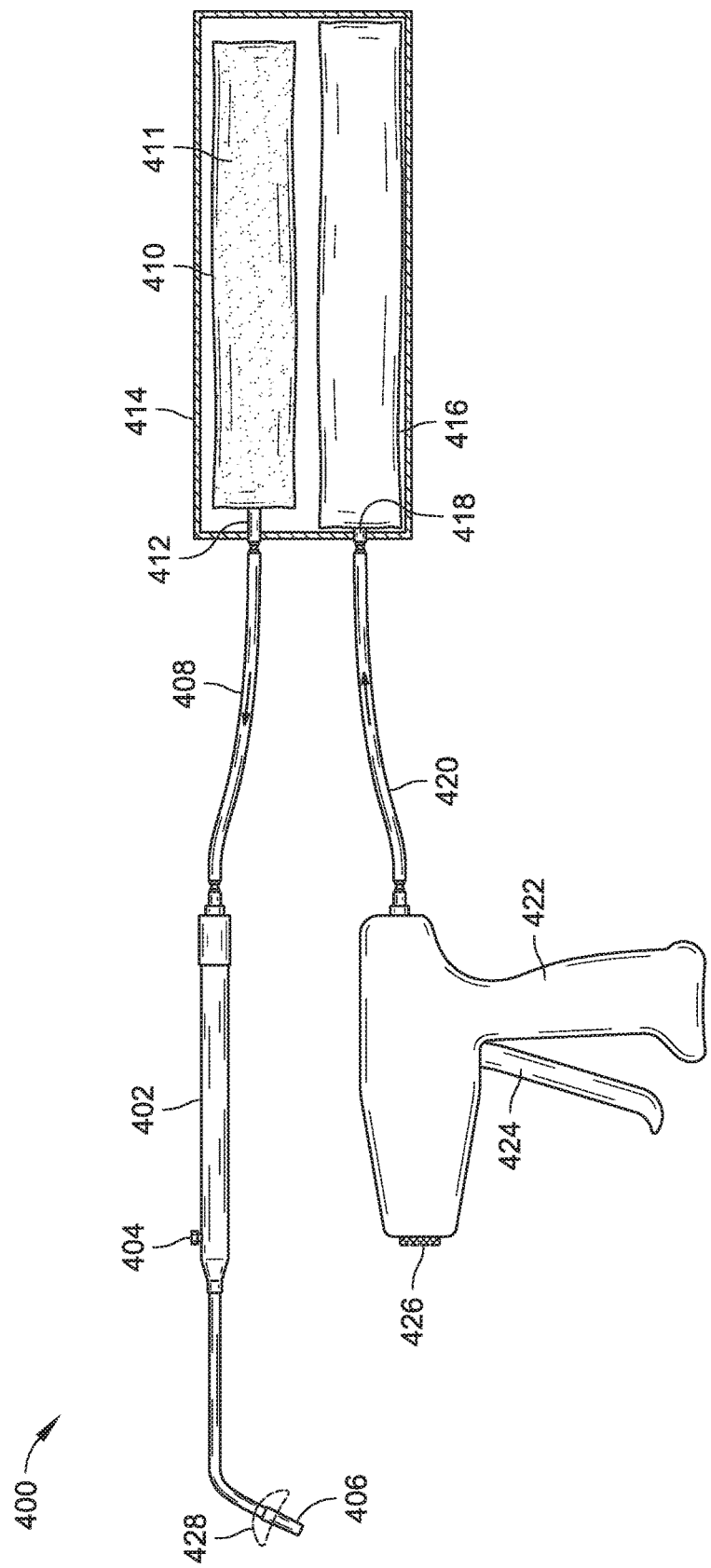
FIG. 4 is a diagrammatic illustration of a wound irrigation system in accordance with an example embodiment of the present disclosure.

Referring to FIG. 4, an irrigation system 400 is described. The irrigation system 400 includes an air-powered irrigation device configured as a handheld dispenser, such as an irrigation wand 402. Pressurized gas for the irrigation wand 402 may be supplied from a portable pressurized gas source, such as a pneumatic hand pump 422. Pressurized gas for the irrigation wand 402 may also be supplied from a replaceable pressurized gas source, such as a pressurized $CO_2$ cartridge. Further, the pressurized gas may be supplied from an in-room source of pressurized gas. In some embodiments, the irrigation wand 402 may have an actuator 404, such as a button or another actuation device (e.g., a trigger), to initiate flow of an irrigation solution 411, e.g., once the air-powered irrigation device has been connected to the pneumatic hand pump 422. The pneumatic hand pump 422 may also include an actuator 424, such as a trigger or another actuation device (e.g., a button), to pressurize an inflatable air bladder 416. Each trigger pull may deliver a measured dose of air into the inflatable air bladder 416.

The irrigation system 400 may include an air line 420 to deliver pressurized gas from the pneumatic hand pump 422 to the inflatable air bladder 416. The air line 420 can be connected to the inflatable air bladder 416 via a fitting 418 such as a barb protruding from a housing 414. The air line 420 forms a fluid path coupling the inflatable air bladder 416 with the pneumatic hand pump 422. The irrigation system 400 may also include an irrigation solution line 408 to deliver the irrigation solution 411 from a deformable container (e.g., an irrigation solution bag 410) holding the irrigation solution 411 to the irrigation wand 402. The irrigation solution line 408 can be connected to the irrigation solution bag 410 via a fitting 412 such as a barb protruding from the housing 414. The housing 414 including the inflatable air bladder 416 and the irrigation solution bag 410 may be reusable. For instance, the irrigation solution bag 410 may be refillable via a connection established with the fitting 412.

The irrigation solution line 408 may be connected to a channel in the irrigation wand 402 (e.g., via a fitting protruding from the irrigation wand 402). The channel forms a fluid path between a nozzle of the irrigation wand 402 and an input of the irrigation wand 402 (e.g., the fitting protruding from the irrigation wand 402). In this manner, the input can be fluidically coupled to the irrigation solution bag 410. In some embodiments, the channel may be formed using medical-grade tubing. In other embodiments, the channel may be formed in and defined by the body of the irrigation wand 402. In some embodiments, one or more air supply lines (e.g., the air line 420) and/or the pneumatic hand pump 422 may include an air filter, such as a filter 426 for filtering air to and/or from the pneumatic hand pump 422 (e.g., to prevent or minimize infiltration of contaminants into the pneumatic hand pump 422, the air line 420, the inflatable air bladder 416, and so forth). It should be noted that by keeping the irrigation solution 411 and the air from the pneumatic hand pump 422 separated, the possibility for introducing contaminated air particles into the irrigation solution 411 may be reduced or eliminated.

Once the inflatable air bladder 416 is pressurized with air, the bladder expands to at least partially deform and pressurize the irrigation solution bag 410, and the operator may start the flow of irrigation solution 411 via a release trigger such as the actuator 404. In some embodiments, the irrigation system 400 may limit the flow of pressurized gas from the pneumatic hand pump 422 to not exceed, for instance, a maximum pressure in pounds per square inch (psi) (e.g., for optimal wound healing). For example, the pneumatic hand pump 422, the air line 420, and/or the inflatable air bladder 416 may include an adjustable pressure release valve or another pressure limiting mechanism. The irrigation system 400 may also include a flow control valve, e.g., using a dial knob or another adjustment mechanism, to control the flow rate of gas from the pneumatic hand pump 422.

In some embodiments, the irrigation wand 402 and a container/bag for holding the irrigation solution 411 may be coupled together in a unitary device. For example, the irrigation solution bag 410 for the irrigation solution 411 may be connected to a posterior end of the irrigation wand 402 to prime the device. The irrigation system 400 may also include a nozzle, such as a spray tip 406 on the irrigation wand 402, for spraying the irrigation solution 411 and/or a splash shield 428 disposed proximate to and at least partially surrounding the nozzle for containing the irrigation solution 411 while it is sprayed from the irrigation wand 402. The spray tip 406 may be one of a number of different interchangeable irrigation tips that provide various spray patterns and/or fluid pressure characteristics when expelling the irrigation solution 411 (e.g., as illustrated in FIGS. 6A through 6D).

Figure 5:
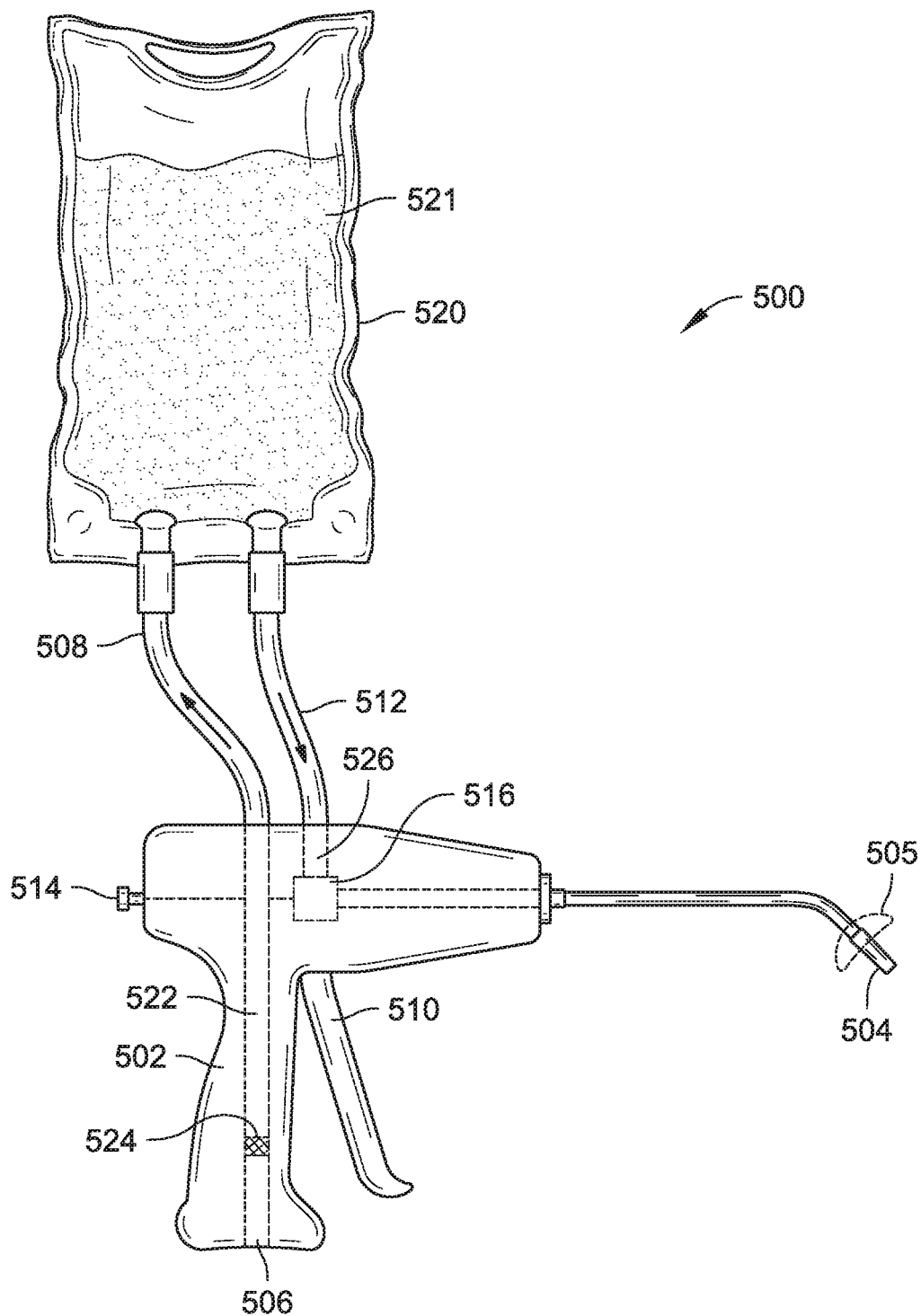
FIG. 5 is a diagrammatic illustration of a wound irrigation system configured as a handheld wound irrigator in accordance with an example embodiment of the present disclosure.
Figure 6B:
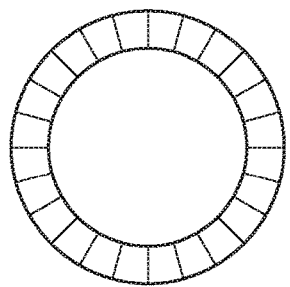
FIG. 6B is a diagrammatic illustration of another spray nozzle tip pattern providing second spray pattern and fluid pressure characteristics in accordance with an example embodiment of the present disclosure.
Figure 6D:
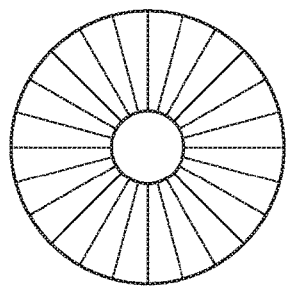
FIG. 6D is a diagrammatic illustration of a spray nozzle tip pattern providing fourth spray pattern and fluid pressure characteristics in accordance with an example embodiment of the present disclosure.
Figure 6A:
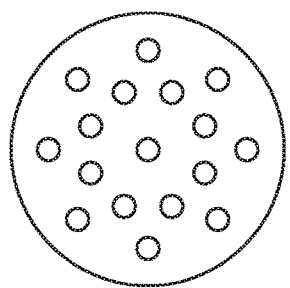
FIG. 6A is a diagrammatic illustration of a spray nozzle tip pattern providing first spray pattern and fluid pressure characteristics in accordance with an example embodiment of the present disclosure.
Figure 6C:
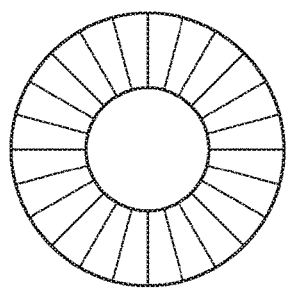
FIG. 6C is a diagrammatic illustration of a spray nozzle tip pattern providing third spray pattern and fluid pressure characteristics in accordance with an example embodiment of the present disclosure.

Referring to FIG. 5, an irrigation system 500 configured as a handheld wound irrigator is described. The irrigation system 500 includes an air-powered irrigation device configured as a handheld dispenser 502. The handheld dispenser 502 may be configured as a portable pressurized gas source, such as a pneumatic hand pump. Pressurized gas for the handheld dispenser 502 may also be supplied from a replaceable pressurized gas source, such as a pressurized $CO_2$ cartridge. Further, the pressurized gas may be supplied from an in-room source of pressurized gas. In some embodiments, the handheld dispenser 502 may have a release trigger such as an actuator 514 configured as a button or another actuation device (e.g., a trigger) to initiate flow of an irrigation solution 521 and selectively dispense the cleansing fluid after increasing the internal pressure of the container. The handheld dispenser 502 may also include an actuator 510, such as a trigger or another actuation device (e.g., a button), to pressurize irrigation solution 521 held in an irrigation solution bag 520. Each trigger pull may deliver a measured dose of air into the irrigation solution bag 520.

The irrigation system 500 may include an air line 508 to deliver pressurized gas from the handheld dispenser 502 to the irrigation solution bag 520 holding the irrigation solution 521. The air line 508 may be connected to a channel 522 in the handheld dispenser 502 (e.g., via fittings such as barbs/Christmas tree connections protruding from the handheld dispenser 502). The air line 508 forms a fluid path coupling the handheld dispenser 502 with the irrigation solution bag 520. The channel 522 can be connected to an air intake port (e.g., an air inlet 506) defined in the handheld dispenser 502. The irrigation system 500 may also include an irrigation solution line 512 to deliver the irrigation solution 521 from the irrigation solution bag 520 to the handheld dispenser 502.

The irrigation solution line 512 may be connected to a channel 526 in the handheld dispenser 502 (e.g., via a fitting such as a barb/Christmas tree connection protruding from the handheld dispenser 502). The channel 526 forms a fluid path between a nozzle of the handheld dispenser 502 and an input of the handheld dispenser 502 (e.g., the fitting protruding from the handheld dispenser 502). In this manner, the input can be fluidically coupled to the irrigation solution bag 520. In some embodiments, the channels 522 and/or 526 may be formed using medical-grade tubing. In other embodiments, the channels 522 and/or 526 may be formed in and defined by the body of the handheld dispenser 502. In some embodiments, one or more air supply lines (e.g., the air line 508) and/or the handheld dispenser 502 may include an air filter, such as a filter 524 in the channel 522 for filtering air to and/or from the handheld dispenser 502 (e.g., to prevent or minimize infiltration of contaminants into the handheld dispenser 502, channels 522 and/or 526, the air line 508, the irrigation solution line 512, the irrigation solution bag 520, and so forth).

Once the irrigation solution bag 520 is pressurized with air, the operator may start the flow of irrigation solution 521 via the actuator 514 on the handheld dispenser 502, which may be connected to, for instance, a flow control valve 516 in the channel 526 for selectively controlling the flow of the irrigation solution 521 through the channel 526 (e.g., controlling when irrigation solution 521 is expelled from the handheld dispenser 502, the rate at which it is expelled, and so on). In other embodiments, once the irrigation solution bag 520 is pressurized with air, the flow of irrigation solution 521 may begin automatically. In some embodiments, flow volume and pressure may depend on a number of trigger presses. The irrigation system 500 may also limit the flow of pressurized gas from the handheld dispenser 502 to not exceed, for instance, a maximum pressure in pounds per square inch (psi) (e.g., for optimal wound healing). For example, the handheld dispenser 502, the air line 508, and/or the irrigation solution bag 520 may include an adjustable pressure release valve or another pressure limiting mechanism. The irrigation system 500 may also include a flow control valve, e.g., using a dial knob or another adjustment mechanism, to control the flow rate of gas from the handheld dispenser 502.

In some embodiments, the handheld dispenser 502 and a container/bag for holding the irrigation solution 521 may be coupled together in a unitary device. For example, the irrigation solution bag 520 for the irrigation solution 521 may be connected to a posterior end of the handheld dispenser 502 to prime the device. The irrigation system 500 may also include a nozzle, such as a spray tip 504 on the handheld dispenser 502, for spraying the irrigation solution 521 and/or a splash shield 505 disposed proximate to and at least partially surrounding the nozzle for containing the irrigation solution 521 while it is sprayed from the handheld dispenser 502. The spray tip 504 may be one of a number of different interchangeable irrigation tips that provide various spray patterns and/or fluid pressure characteristics when expelling the irrigation solution 521 (e.g., as illustrated in FIGS. 6A through 6D).

In embodiments, components of the irrigation systems 100, 200, 300, 400, and/or 500 may be constructed using various medical-grade materials, including, but not necessarily limited to: metal materials (e.g., surgical stainless steel), plastic materials, resin materials, and so forth. As described herein, tools constructed using metal materials, such as stainless steel, may be reused after cleaning (e.g., using an autoclave or another medical cleaning device). In some embodiments, tools constructed of plastic and/or resin materials may be cleanable and/or disposable. For example, the handheld dispensers 102, 202, and/or 502, and/or the irrigation wands 302, and/or 402, may be formed using a plastic injection molding process or a resin molding process and may be disposed of after a limited number of uses (e.g., after one use). This may aid in facilitating equipment sterility. Similarly, other components, such as the air lines 116, 118, 120, 214, 216, 310, 322, 408, 420, 508, and/or 512, channels formed using tubing extending through the handheld dispensers 102, 202, and/or 502, and/or channels formed using tubing extending through the irrigation wands 302, and/or 402, and so on, may also be cleanable and/or disposable.

In embodiments, components of the irrigation systems 100, 200, 300, 400, and/or 500, and/or the irrigation solutions 123, 219, 317, 411, and/or 521 may be heated and/or cooled by a heating and/or cooling element. For example, a battery or another power source may be used to power heating and/or cooling of the channels 104, 106, 108, 204, 522, and/or 526, the air lines 116, 118, 216, 322, 420, and/or 508, the irrigation solution lines 120, 214, 310, 408, and/or 512, the containers 122, 218, and/or 316, the irrigation solution bags 410 and/or 520, the irrigation solutions 123, 219, 317, 411, and/or 521, and so forth (e.g., for a decontamination procedure specifying the use of a warm or cool liquid). In some embodiments, a cold liquid may be furnished for nerve gas decontamination. In an example, the air line 216 described with reference to FIG. 2 may be routed proximate to (e.g., in contact with) the $CO_2$ cartridge 208 to cool the air line 216 as the carbon dioxide is expelled from the cartridge. In another example, a thermoelectric cooling and/or heating device, such as a Peltier cooling and/or heating device, may be used to heat and/or cool various components of the irrigation systems 100, 200, 300, 400, and/or 500, the irrigation solutions 123, 219, 317, 411, and/or 521, and so on.

Although the subject matter has been described in language specific to structural features and/or process operations, it is to be understood that the subject matter defined in the appended claims is not necessarily limited to the specific features or acts described above. Rather, the specific features and acts described above are disclosed as example forms of implementing the claims.

What is claimed is:

1. A wound irrigation system, comprising:
a handheld dispenser having a nozzle for dispensing a cleansing fluid, the handheld dispenser defining a first fluid path between the nozzle and an input of the handheld dispenser, the input configured to be fluidically coupled to a container of the cleansing fluid; and
a second fluid path configured to couple the container with a gas source for pressurizing the container,
wherein the handheld dispenser defines at least a portion of the second fluid path and an aperture disposed between a first portion of the second fluid path and a second portion of the second fluid path, the aperture configured to be at least partially closed in order to increase an internal pressure of the container.

2. The wound irrigation system as recited in claim 1, wherein closing the aperture causes the nozzle to dispense the cleansing fluid at a fluid pressure ranging between about eight pounds per square inch (8 psi) and about twenty pounds per square inch (20 psi).

3. The wound irrigation system as recited in claim 1, wherein the handheld dispenser includes a flow rate controller disposed between a first portion of the second fluid path and a second portion of the second fluid path.

4. The wound irrigation system as recited in claim 3, wherein the flow rate controller comprises a roller configured to at least partially narrow or widen a segment of the second fluid path when the roller translates over the segment in a first direction or a second direction, the segment disposed between the first portion of the second fluid path and the second portion of the second fluid path.

5. The wound irrigation system as recited in claim 3, wherein the flow rate controller is configured to cause the nozzle to dispense the cleansing fluid at a plurality of fluid pressures ranging between about eight pounds per square inch (8 psi) and about twenty pounds per square inch (20 psi).

6. The wound irrigation system as recited in claim 1, wherein the second fluid path is defined between a second input of the handheld dispenser and an output of the handheld dispenser, the second input configured to be coupled to the gas source and the output configured to be coupled to the container.

7. The wound irrigation system as recited in claim 1, wherein the gas source comprises a portable gas source, and the handheld dispenser includes a holster configured to receive the portable gas source.

8. The wound irrigation system as recited in claim 7, wherein the portable gas source comprises a $CO_2$ cartridge.

9. The wound irrigation system as recited in claim 1, further comprising a shield proximate to and at least partially surrounding the nozzle.

10. The wound irrigation system as recited in claim 1, wherein the nozzle comprises an interchangeable nozzle selected from a set of interchangeable nozzles that provide a plurality of different fluid pressure characteristics.

11. The wound irrigation system as recited in claim 1, further comprising a filter disposed along the second fluid path.

12. The wound irrigation system as recited in claim 1, further comprising a pressure release valve disposed along the second fluid path or coupled to the container, the pressure release valve configured to prevent an internal pressure of the container from exceeding a threshold pressure.

13. The wound irrigation system as recited in claim 12, wherein the threshold pressure is at least twenty pounds per square inch (20 psi).

14. The wound irrigation system as recited in claim 1, wherein the gas source is configured to supply a continuous flow of gas.

15. The wound irrigation system as recited in claim 14, further comprising a control valve configured to control a flow rate of the continuous flow of gas from the gas source.

16. A wound irrigation system, comprising:
a handheld dispenser having a nozzle for dispensing a cleansing fluid, the handheld dispenser defining a first fluid path between the nozzle and an input of the handheld dispenser, the input configured to be fluidically coupled to a container of the cleansing fluid; and
a second fluid path configured to couple the container with a gas source for pressurizing the container,
wherein the handheld dispenser defines at least a portion of the second fluid path and includes a flow rate controller disposed between a first portion of the second fluid path and a second portion of the second fluid path, the flow rate controller comprising a roller configured to at least partially narrow or widen a segment of the second fluid path when the roller translates over the segment in a first direction or a second direction, the segment disposed between the first portion of the second fluid path and the second portion of the second fluid path.

17. The wound irrigation system as recited in claim 16, wherein the flow rate controller is configured to cause the nozzle to dispense the cleansing fluid at a plurality of fluid pressures ranging between about eight pounds per square inch (8 psi) and about twenty pounds per square inch (20 psi).

18. The wound irrigation system as recited in claim 16, wherein the second fluid path is defined between a second input of the handheld dispenser and an output of the handheld dispenser, the second input configured to be coupled to the gas source and the output configured to be coupled to the container.

19. The wound irrigation system as recited in claim 16, wherein the gas source is configured to supply a continuous flow of gas.

20. The wound irrigation system as recited in claim 19, further comprising a control valve configured to control a flow rate of the continuous flow of gas from the gas source.

\* \* \* \* \*